US00PP34268P2

(12) United States Plant Patent
Ding et al.

(10) Patent No.: US PP34,268 P2
(45) Date of Patent: May 24, 2022

(54) ***NELUMBO* 'NANZHOU XUEFENG'**

(50) Latin Name: *Nelumbo nucifera*
Varietal Denomination: NANZHAO XUEFENG

(71) Applicants: Yuesheng Ding, Nanjing (CN); Mei Tong, Nanjing (CN); Lei Xie, Nanjing (CN); Xianding Cao, Nanjing (CN); Zhaoqin Tong, Nanjing (CN)

(72) Inventors: Yuesheng Ding, Nanjing (CN); Mei Tong, Nanjing (CN); Lei Xie, Nanjing (CN); Xianding Cao, Nanjing (CN); Zhaoqin Tong, Nanjing (CN)

( * ) Notice: Subject to any disclaimer, the term of this patent is extended or adjusted under 35 U.S.C. 154(b) by 0 days.

(21) Appl. No.: 17/554,347

(22) Filed: Dec. 17, 2021

(51) Int. Cl.
*A01H 5/02* (2018.01)

(52) U.S. Cl.
USPC ..... Plt./342

(58) Field of Classification Search
USPC ..... Plt./342
See application file for complete search history.

*Primary Examiner* — Annette H Para

(57) ABSTRACT

A new and distinct cultivar of *Nelumbo* plant named 'NANZHAO XUEFENG' is disclosed, characterized by petals are mainly white with red-purple outer tips, and yellow bases. Flowers have a distinctly hemispherical form, composed of a double whorl of outer petals and a distinctive mounded center made up of a large number of whorled petals and petaloids. The new variety is useful as both an ornamental plant and for cut flower production.

3 Drawing Sheets

Latin name of the genus and species: *Nelumbo nucifera*.
Variety denomination: 'NANZHAO XUEFENG'.

BACKGROUND OF THE INVENTION

The new cultivar, *Nelumbo* 'NANZHAO XUEFENG', is the product of a planned breeding program. The new variety originated from a cross pollination of the unpatented, seed parent, *Nelumbo* 'Yuluo Huatai' with the pollen parent the unpatented *Nelumbo* 'Juwuba'. The cross pollination was made during July of 2018 in in Nanjing, Jiangsu province, China at a research nursery. The new cultivar 'NANZHAO XUEFENG' was selected in June of 2019 at the same location.

Asexual reproduction of the new cultivar 'NANZHAO XUEFENG' was first performed by root division in in Jiangsu province, China at a research nursery during April of 2020. *Nelumbo* 'NANZHAO XUEFENG' has since produced multiple generations and has shown that the unique features of this cultivar are stable and reproduced true to type.

SUMMARY OF THE INVENTION

The cultivar 'NANZHAO XUEFENG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NANZHAO XUEFENG'. These characteristics in combination distinguish 'NANZHAO XUEFENG' as a new and distinct *Nelumbo* cultivar:

1. Fully double-whorled outer petals.
2. Multi-colored flower composed of a primarily white petal, red-purple apex, and yellow base.
3. Mounded-whorl formation of central petals forming a hemispherical flower form.

4. Flowering occurring from mid-June to late August.
5. Individual lowers last 6 to 7 days on plant.

PARENTAL COMPARISON

Plants of the new cultivar 'NANZHAO XUEFENG' are similar to plants of the seed parent in most horticultural characteristics. However, plants of the new cultivar 'NANZHAO XUEFENG' differ in the following:

1. 'NANZHAO XUEFENG' produces more petals per flower than the seed parent.
2. Flower color of 'NANZHAO XUEFENG' is a deeper red-purple at the tip, and a paler yellow base than the flower color of the seed parent.
3. Flower form of 'NANZHAO XUEFENG' is hemispherical, with a strong, mounded center; the flower form of the seed parent is convex.
4. 'NANZHAO XUEFENG' produces larger flowers than the seed parent.
5. 'NANZHAO XUEFENG' has a longer flowering period than the seed parent.
6. 'NANZHAO XUEFENG' sets a scant amount of seed; the seed parent sets a moderate amount of seed.

Plants of the new cultivar 'NANZHAO XUEFENG' are similar to the pollen parent in most horticultural characteristics. However, plants of the new cultivar 'NANZHAO XUEFENG' differ in the following:

1. 'NANZHAO XUEFENG' produces more petals per flower than the pollen parent.
2. Flower color of 'NANZHAO XUEFENG' is a deeper red-purple at the tip, and a paler yellow base than the flower color of the pollen parent.
3. 'NANZHAO XUEFENG' produces larger flowers than the pollen parent.
4. 'NANZHAO XUEFENG' has a higher number of stamens than the pollen parent.

COMMERCIAL COMPARISON

The new cultivar 'NANZHAO XUEFENG' can be compared to the unpatented commercial variety *Nelumbo*

'Zhufeng Cuiying'. Plants of the new cultivar 'NANZHAO XUEFENG' differ in the following:

1. Flowers of 'NANZHAO XUEFENG' produce more petals than flowers of 'Zhufeng Cuiying'.
2. Flower colors of 'NANZHAO XUEFENG' are white, red-purple, and yellow; flower colors of this comparator are green-white and yellow.
3. Flower form of 'NANZHAO XUEFENG' is hemispherical; flower form of 'Zhufeng Cuiying' is flattened.
4. 'NANZHAO XUEFENG' has a partially vesiculated carpel, while this comparator has a fully petaloid carpel.
5. Flower bud shape of 'NANZHAO XUEFENG' is broad oval; flower bud shape of this comparator is oval.

BRIEF DESCRIPTION OF THE PHOTOGRAPHS

The accompanying photographs illustrate in full color typical plants of 'NANZHAO XUEFENG' grown outdoors, in a pond, in Jiangsu province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Nelumbo* plant. Temperatures ranged from approximately 13° C. to 28° C. night and about 16° C. to 34° C. during the day. No artificial light, photoperiodic treatments or chemical treatments were given to the plants.

DETAILED BOTANICAL DESCRIPTION

Figure 1:
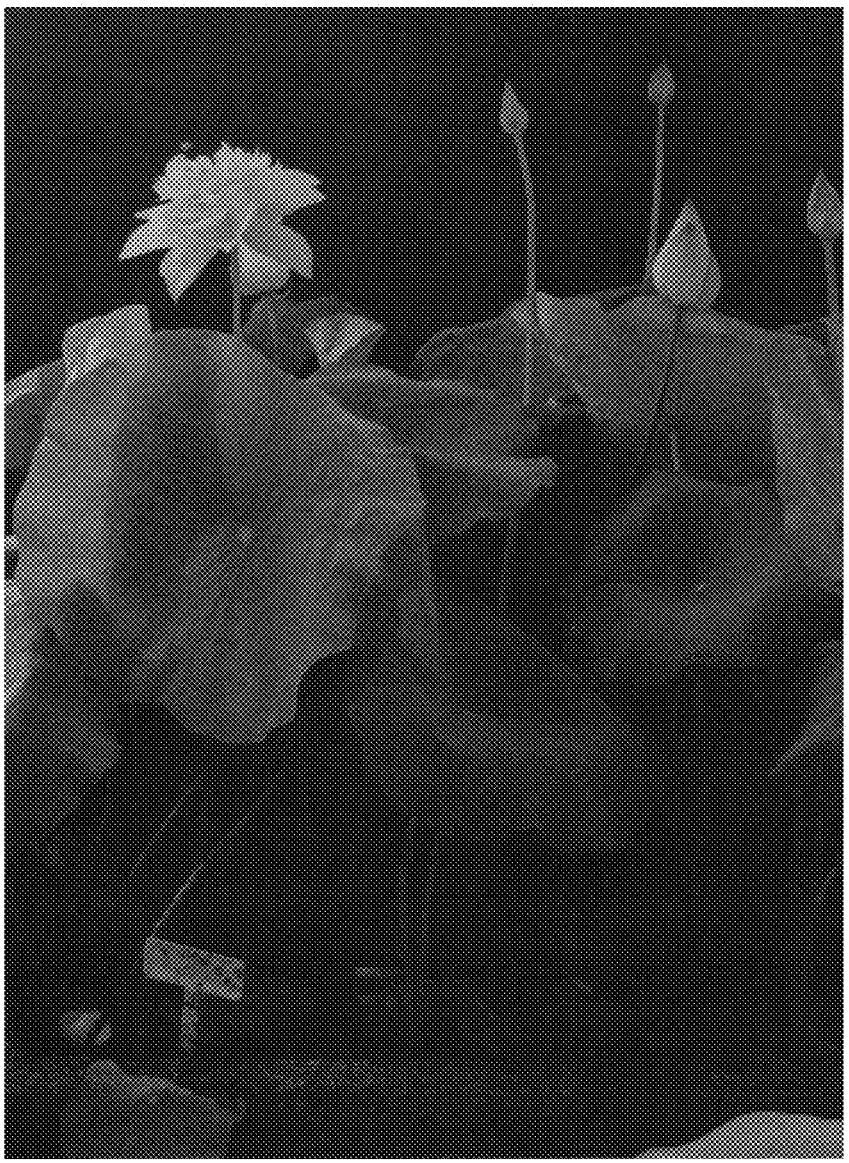
FIG. 1 illustrates in full color typical flowering plants of *Nelumbo* 'NANZHAO XUEFENG' at approximately 1 year of age.
Figure 2:
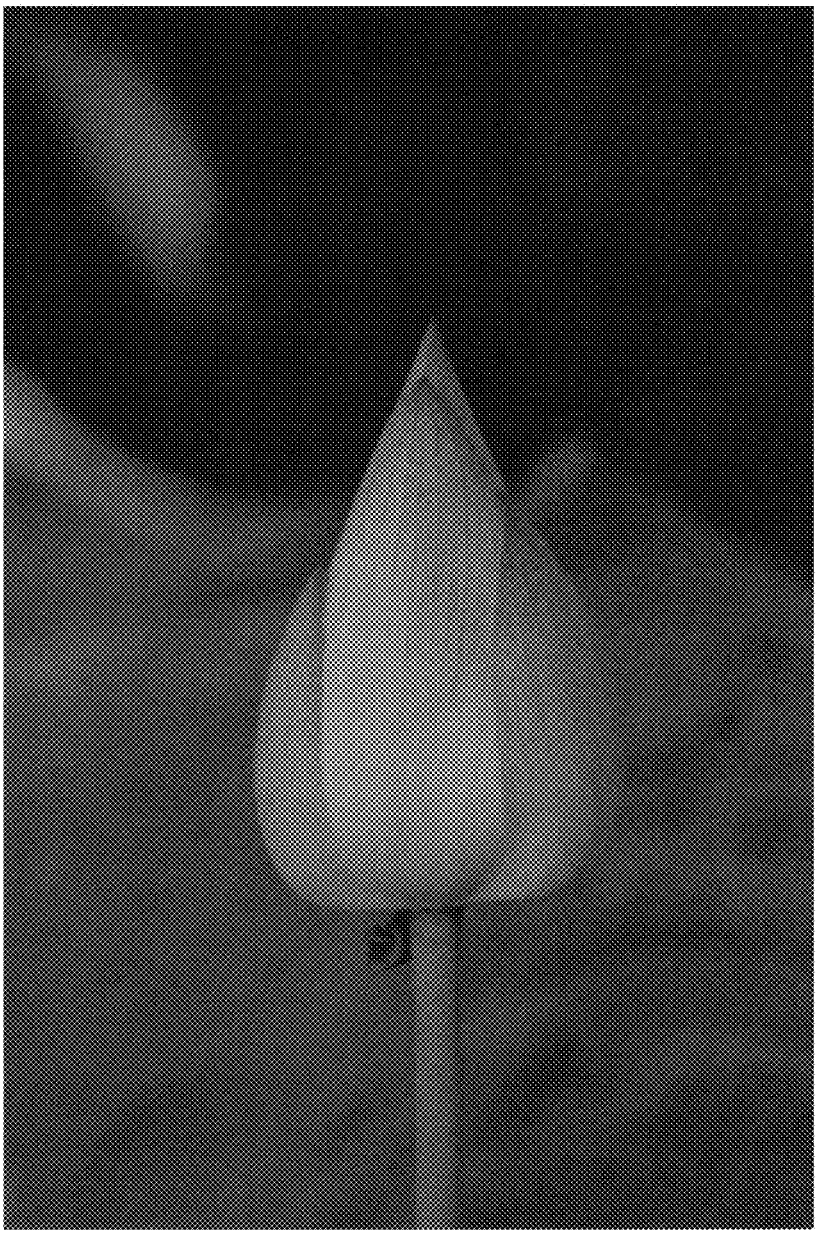
FIG. 2 illustrates in full color a typical flower bud of *Nelumbo* 'NANZHAO XUEFENG'.
Figure 3:
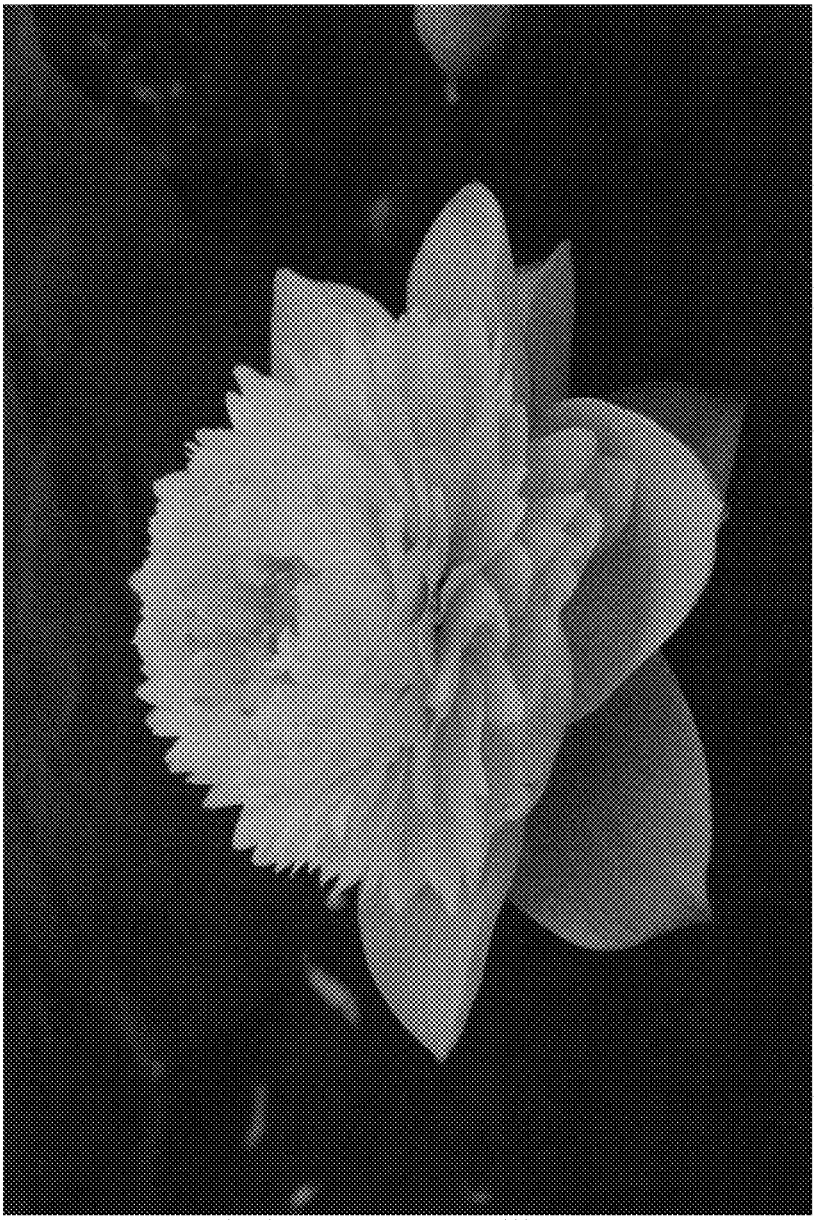
FIG. 3 illustrates in full color typical fully open flower of *Nelumbo* 'NANZHAO XUEFENG'.

In the following description, color references are made to The Royal Horticultural Society Colour Chart, 2019, except where general terms of ordinary dictionary significance are used. The following observations and measurements describe 'NANZHAO XUEFENG' plants grown in an outdoor pond in Jiangsu province, China. Average day temperature range was around 16° C. to 34° C.; average night temperature ranged around 13° C. to 28° C. No artificial light, photoperiodic treatments or chemical treatments were given to the plants. Natural light conditions were full sunlight. Measurements and numerical values represent averages of typical plant types. Measurements were taken during June to August of 2021.

Botanical classification: *Nelumbo nucifera* 'NANZHAO XUEFENG'.

PROPAGATION

Type of propagation typically used: Root divisions.

Root description: Adventitious roots at the rhizome node. Moderately dense, moderately branching, medium thickness, fleshy texture. White in color, not accurately described with R.H.S. chart.

PLANT

Age of plant described: 1 year.

Container size of the plant described: In a pond of approximately 4 meters in length, 0.9 meters in width, and 25 cm in depth.

Growth habit: Heliophilous.

Height: Average 62 to 80 cm from soil to top of foliar plane; 83 to 110 cm from soil to top of floral plane.

Plant spread: Approximately 90 to 130 cm.

Growth rate: Moderate.

Plant vigor: High.

Branching habit: Sympodial.

Primary branches per plant: 5 to 10.

Secondary branches per primary lateral branch: 3 to 5.

Lateral branch length: 80 to 120 cm.

Lateral branch diameter: 2.5 to 4 cm.

Internode length: 15 to 20 cm.

Stem:

*Shape/appearance*.—Rhizomatous, nodose, cylindrical.

*Aspect*.—Horizontal underground growth.

*Strength*.—Weak.

*Color*.—Developing: Near RHS Yellow-White 158C. At Internodes: Near RHS Yellow-White 158C. Developed: Near RHS Greyed-Yellow 162C.

*Pubescence*.—None.

*Luster*.—Matte.

FOLIAGE

Leaf:

*Arrangement*.—Single leaf ranked, before and after flowering.

*Average length*.—Average 40 to 58 cm.

*Average width*.—34 to 50 cm.

*Shape of blade*.—Orbicular.

*Apex*.—Dimple.

*Base*.—Peltate.

*Margin*.—Entire, slightly undulate.

*Texture of top surface*.—Smooth.

*Texture of bottom surface*.—Smooth, cancellate.

*Color*.—Young foliage upper side: RHS Yellow-Green 143C. Young foliage, under side: RHS Yellow-Green 148C. Mature foliage upper side: RHS Green 137B. Mature foliage, under side: RHS Yellow-Green N148D. Fall foliage upper side: RHS Yellow-Green N151D, centrally blotched Green 137B. Fall foliage, under side: RHS Yellow Green N148D streaked 151D.

*Venation*.—Type: Reticulate. Venation color upper side: RHS Green 138A. Venation color under side: RHS Yellow-Green 147C.

Petiole:

*Average length*.—Average range 58 cm to 75 cm.

*Average diameter*.—Average range 0.9 mm to 1.3 cm.

*Color*.—Upper surface: RHS Green 143C. Lower surface: RHS Green 143C.

*Texture*.—Semi-woody, stiff, inside have vertical hollow and latex.

*Luster*.—Weak.

FLOWER

Natural flowering season: June through August.

Flower type and habit: Single occurring rotate, hemispherical flowers composed of a double whorl of outer petals and mounded center composed of whorls of petals and petaloids. Upright facing.

Flowers per plant: 12 to 18 flowers and buds per square meter produced per year. Free flowering.
Flower longevity on plant: 7 to 8 days. Self-cleaning.
Flower longevity as a cut flower: Less than 4 days.
Flower size:
*Height*.—Approximately 19 to 25 cm.
*Width*.—Approximately 21 to 26 cm.
*Depth*.—9 to 12 cm.
Flower shape: Petal-piled, ball-like.
Bud:
*Shape*.—Broad ovate.
*Length*.—Approximately 5.6 to 8.5 cm.
*Diameter*.—Approximately 5.6 to 8.5 cm.
*Luster*.—None.
*Color*.—Upper: Main color: Yellow-Green 145C and 145D. Apical margin near Red-Purple 59B. Margin flushed 59C. Veins strongly flushed 59C near margins. Red-Purple flush of veins fading descending from margin.
Petals:
*Arrangement*.—Whorled.
*Quantity*.—475 to 507 per flower.
*Number of whorls*.—Average 15, including 2 outer whorls of larger petals.
*Fused*.—No.
*Margin*.—Entire.
*Shape*.—Outer whorls of petals: broad obovate; inner whorls obovate-lanceolate.
*Apex*.—Acuminate.
*Base*.—Truncate.
*Texture*.—Papery, all surfaces.
*Rugosity*.—Smooth and weak, under side only.
*Luster*.—Weak, both sides.
*Petal length*.—4.4 to 13.2 cm.
*Petal width*.—0.9 to 9.2 cm.
*Color*.—When Opening: Upper Surface: Main: RHS White 155B; Outer whorl tip: Red-Purple 58A; Base: Yellow 3D. Under Surface: Main: RHS White 155B; Outer whorl tip: Red-Purple 58A; Base: Yellow 2D. Fully Opened: Upper Surface: Main: RHS White 155B; Outer whorl tip: Red-Purple 58A; Base: Yellow 4B; Venation: White 155A. Under Surface: Main: RHS White 155B; Outer whorl tip: Red-Purple 58A; Base: Yellow 4D; Venation: White 155A. Fading: Upper Surface: Main: RHS White NN155A; Base: Yellow 4C. Under Surface: Main: RHS White NN155A; Base: Yellow 4D.
Petaloids:
*Arrangement*.—Whorled.
*Quantity*.—475 per flower.
*Number of whorls*.—12.
*Length*.—4.4 to 8.1 cm.
*Width*.—0.9 to 3 cm.
*Shape*.—Obovate-lanceolate.
*Margin*.—Entire.
*Apex*.—Mucronate.
*Base*.—Wedge.
*Texture*.—Papery, both surfaces.
*Rugosity*.—Smooth, not rugose.
*Luster*.—Weak, both sides.
*Color*.—When opening: Upper surface: Main: RUS White 155B; Base: Yellow 3C. Under surface: Main: RHS White 155B: Base: Yellow 3D. Fully opened: Upper surface: Main: RHS White 155D; Base: Yellow 3D; Venation: White 155D. Under surface: Main: RHS White 155D; Base: Yellow 4B; Venation: Red-Purple 63D. Fading: Upper surface: Main: RHS White NN155A; Base: Yellow 4C. Under surface: Main: RHS White NN155A; Base: Yellow 4D.
Sepals:
*Quantity*.—8.
*Arrangement*.—Verticillate.
*Calyx shape*.—Oval.
*Fused*.—No.
*Number of whorls*.—2.
*Length*.—3.5 to 10 cm.
*Width*.—0.6 to 5.8 cm.
*Shape*.—Broad obovate.
*Apex*.—Acuminate.
*Margin*.—Entire.
*Base*.—Truncate.
*Texture*.—Papery, both sides.
*Luster*.—Weak, both sides.
*Color*.—When Opening: Upper Surface: Tip: RHS Red-Purple 58A; Base: Green-White 157D. Under Surface: RHS Yellow-Green N144C. Fully Opened: Upper Surface: Tip: RHS Red-Purple 58A; Base: Green-White 157D. Under Surface: RHS Yellow-Green 145A.
Fragrance: Moderate sandalwood scent.
Pedicel:
*Length*.—Average 79 to 106 cm.
*Diameter*.—Average 8 to 10 mm.
*Strength*.—Medium, stout.
*Texture*.—Semi-woody, stiff, inside vertical hollow and latex.
*Luster*.—Weak.
*Color*.—RHS Green 143A.

REPRODUCTIVE ORGANS

Stamens: (Androecium).
*Number*.—Average 101 to 138.
*Filament length*.—Approximately 13 to 14 mm.
*Filament color*.—Near RHS Yellow 9B.
*Anther length*.—12 to 14 mm.
*Anther width*.—1 to 1.5 mm.
*Anther color*.—Near RHS Yellow 12A.
*Anther shape*.—Bar.
*Pollen quantity*.—Moderate.
*Pollen color*.—Near RHS Yellow 12A.
Pistil: (Gynoecium).
*Number*.—Average range 11 to 19.
*Length*.—16 mm.
*Stigma*.—Shape: Circular. Color: Near RHS Yellow 4A. Style Length: 1 to 2 mm. Style Diameter: 2 to 3 mm. Style Color: Near RHS Yellow 4D. Ovary Color: Near RHS Yellow 4D.

OTHER CHARACTERISTICS

Seeds: 1 to 2 per flower.
*Length*.—1.8 to 2.5 cm.
*Diameter*.—1.2 to 1.4 cm.
*Texture*.—Smooth.
*Color*.—Near RHS Brown 200A.
Fruit: 24 to 36 per plant.
*Length*.—3.8 to 4.6 cm.
*Diameter*.—5.7 to 7.3 cm.
*Texture*.—Smooth.

*Color*.—Near RHS Yellow-Green N144B, turning N144B then near Grey-Brown N199C.

*Taste*.—None.

*Days to ripen*.—21 to 40 days.

*Root structures*.—Rhizomes. Shape: Cylindrical with nodes, expanded in winter. Diameter: 2 to 4 cm. Texture: Fleshy. Color: Near White 155B.

Temperature tolerance: Tolerates temperatures from approximately −10° C. to at least 40° C. High tolerance to rain. Moderate tolerance to wind.

Disease/pest resistance: Moderate resistance and susceptibility to normal diseases of *Nelumbo* observed. Moderate resistance and susceptibility to normal pests of *Nelumbo* observed.

What is claimed is:

1. A new and distinct cultivar of *Nelumbo* plant named 'NANZHAO XUEFENG' as herein illustrated and described.

* * * * *